United States Patent [19]

Schlie

[11] Patent Number: 5,200,986
[45] Date of Patent: Apr. 6, 1993

[54] X-RAY EXAMINATION APPARATUS AND FILTER MEANS FOR USE IN SUCH X-RAY

[75] Inventor: Harald Schlie, Hamburg, Fed. Rep. of Germany

[73] Assignee: U.S. Philips Corp., New York, N.Y.

[21] Appl. No.: 864,109

[22] Filed: Apr. 6, 1992

[30] Foreign Application Priority Data

Apr. 12, 1991 [EP] European Pat. Off. ........ 91200860.4

[51] Int. Cl.⁵ .............................................. G21K 3/00
[52] U.S. Cl. ..................................... 378/156; 378/159
[58] Field of Search ................................. 378/156, 159

[56] References Cited

U.S. PATENT DOCUMENTS

| 4,670,896 | 6/1987 | Klausz | 378/156 |
| 5,086,444 | 2/1992 | Bartman | 378/152 |
| 5,107,529 | 4/1992 | Boone | 378/156 |

Primary Examiner—Craig E. Church
Attorney, Agent, or Firm—Jack D. Slobod

[57] ABSTRACT

In an x-ray examination apparatus comprising
a frame (2) to which are connected an x-ray source (3) for emission of an x-ray beam and an x-ray detector (5) that is placed opposite the x-ray source, and
filter means (31) that are placed between the x-ray source (3) and the x-ray detector (5) the filter means (31) comprising an x-ray absorbing filter body (33) and drive means for positioning the filter body in the x-ray beam, the drive means comprise two disk-shaped holding members between which the filter body is placed. The filter body is in a pivot-point pivotably fixed to one holding member and is provided with a pawl that engages a curved radial groove in the second holding member. By joint rotation of the holding members the filter body is translated in the x-ray beam whereas by rotation of one of the holding members only, the curved radial groove causes the filter body to rotate in the x-ray beam.

18 Claims, 3 Drawing Sheets

X-RAY EXAMINATION APPARATUS AND FILTER MEANS FOR USE IN SUCH X-RAY

BACKGROUND OF THE INVENTION

1. Field of the Invention

The invention relates to an x-ray examination apparatus comprising a frame to which are connected an x-ray source for emission of an x-ray beam and an x-ray detector that is placed opposite the x-ray source, and filter means that are placed between the x-ray source and the x-ray detector, the filter means comprising an x-ray absorbing filter body and drive means for positioning the filter body in the x-ray beam.

The invention also relates to a filter means for use in such an x-ray examination apparatus.

2. Description of the Prior Art

An x-ray examination apparatus of the above-mentioned kind is known from the European Patent EP-B1-157 688 which corresponds to U.S. Pat. No. 4,670,896.

From the above-mentioned patent it is known that when objects having a mutually different x-ray absorption appear in the same x-ray image, such as heart and lungs, the x-ray image shows very bright areas next to very dark areas. Structures in the x-ray image having only a small difference in contrast falling within these areas are difficult to observe. By placing a wedge-shaped filter body in the x-ray beam such that the x-ray beam is attenuated in the areas of high transmissivity, the average contrast in the picture is reduced, such that the dynamic range of the x-ray image can be adjusted to cover the range of absorption values of the details that are of interest. Thereto first an x-ray image is made that is optically projected onto the patient. By placing wedge-shaped filter bodies, consisting for instance of plastic and lead, having an optical absorption corresponding with the x-ray absorption of the filter body in the light path, a visual indication of the filter position is obtained. After the filter bodies are in the desired position the final x-ray picture is taken. In an x-ray examination apparatus of the above-mentioned kind, the x-ray beam is collimated by two pairs of x-ray absorbing shutters the projection of which onto the patient determines the field of view. These shutters are movably mounted within a housing that is close to the x-ray source. In the same housing a mirror is present to project light onto the patient from a position corresponding to the position of the x-ray source such as to obtain an optical indication of the field of view. An extra filter that can be placed into the x-ray beam is preferably mounted in the same housing with the mirror and the collimating lead shutters and should therefor take up little space.

SUMMARY OF THE INVENTION

It is therefor an object of the invention to provide for an x-ray examination apparatus of the above-mentioned kind, in which filter means are provided that take up as little space as possible. It is also an object of the invention to provide for a filter means of simple, relatively cheap and failsafe design.

Thereto an x-ray examination apparatus in accordance with the invention is characterized in that the drive means comprise two holding members having a central opening positioned around a central ray connecting the x-ray source and the x-ray detector, the filter body being placed between the holding members and being movably connected thereto via a guiding means, a motor coupled to at least one holding member for rotation of the holding member around the central ray and coupling means for coupling and uncoupling the holding members joint rotation of the holding members around the central ray causing the filter body to be fixed relative to the holding members, rotation of one of the holding members with respect to the other holding member causing the filter body to move relative to the holding members via the guiding means.

Because for both rotation and translation of the filter body in the x-ray beam one single motor is used, the filter means take up less space than would have been the case if two separate motors were used. Because by simple mechanical means both rotation and translation of the filter body are performed, the number of components of the filter means is kept small thus, reducing the price of the filter means.

An embodiment of an x-ray examination apparatus in accordance with the invention is characterized in that the holding members and the filter body are plate-shaped, the filter body being connected to a first holding member in a pivot-point such as to be pivotable in a plane parallel to the holding members, the guiding means comprising a pawl which is provided on the filter body or the second holding member and a groove in the second holding member or in the filter body in which groove the pawl is guided.

When the holding members are rotated together, the filter body is clamped between the holding members and rotates with the holding members around the central ray. When the holding members rotate with respect to one another, the pawl and the groove force the filter body to pivot around the pivot point and move into the central opening toward or away from central ray depending on the direction of rotation of the holding members. The pawl can be provided on the filter body, in which case the groove is provided in the second holding member that faces the side of the filter body having the pawl. The groove is curved and extends in a radial direction. The pawl can also be provided on the second holding member in which case the groove runs in the filter body.

Another embodiment of an x-ray examination apparatus in accordance with the invention is characterized in that the holding members have a toothed circular circumference.

The holding members can be coupled to a gearwheel of the motor either directly or via a transmission gear. Since the connection requires no intermediate transmission means such as pulleys, chains or drive belts, the number of components of the filter means can remain relatively small.

Another embodiment of an x-ray examination apparatus in accordance with the invention is characterized in that the coupling means comprise a friction member for transmission of rotation of one holding member to the other holding member and a brake for locking one of the holding members.

Both holding members are for example each connected to a gearwheel, one of which is driven by the motor. Via a friction member the gearwheels of both the holding members are coupled, such that rotation of the gearwheel that is directly driven by the motor is transferred to the second gearwheel and both holding members rotate together. By actuation of the brake, that can be an electromagnetic clutch, the gearwheel of the holding member that is not directly driven by the motor can be blocked. Since the force exerted by the friction member is not large enough to cause rotation of said blocked holding member, only the holding member that is directly driven by the motor is able to rotate.

Another embodiment of an x-ray examination apparatus in accordance with the invention is characterized in that two filter means are provided as one integral unit which is placed near the x-ray source.

By using two filter means in the same housing, a large number of areas of different geometries can be covered in an x-ray image by the two filter bodies.

BRIEF DESCRIPTION OF THE DRAWING

Some preferred embodiments of an x-ray examination apparatus and filter means according to the invention will be described in detail hereinafter with reference to the accompanying drawings.

DESCRIPTION OF THE PREFERRED EMBODIMENT

Figure 1:
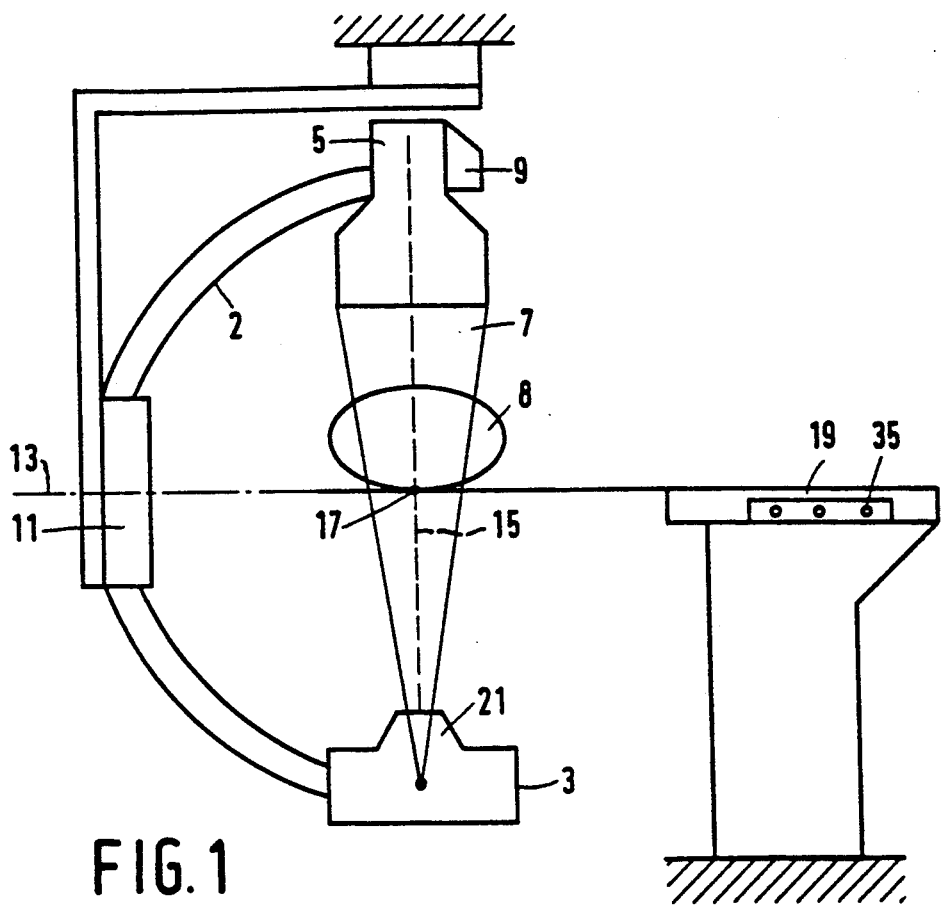
FIG. 1 shows an x-ray examination apparatus.

FIG. 1 shows an x-ray examination apparatus comprising a C-shaped frame 2 to which are connected an x-ray source 3 and an x-ray image intensifier tube 5. The x-ray source 3 emits a beam of x-rays 7 which after passing through a patient body 8 is detected on the entrance screen of the image intensifier tube 5. In the entrance screen, that comprises for instance CsI, a light image is formed which impinges on a photocathode and liberates electrons therefrom. The electrons are accelerated through a potential difference of for instance 20 kV and impinge on an output screen containing phosphorus to form a light image with increased intensity. The light image on the output screen of the image intensifier tube 5 is detected with a television camera 9 that forms a video signal which is displayed on a television monitor. The C-shaped frame 2 can move in a circumferential direction within a supporting member 11, the supporting member 11 being rotatable around an axis 13. By rotation of the frame 2 in the circumferential direction or by rotation of the supporting member 11 around the axis 13, a central ray 15 connecting the x-ray source 3 and the x-ray image intensifier tube 5 rotates around an isocenter 17. In an x-ray image the isocenter 11 always occupies the same position irrespective of the position of the frame 2. A table height of a patient table 19 is usually chosen such as to place an area of interest within a patient 8 in the isocenter 17. Close to the x-ray source 3 a collimating unit 21 is placed which contains lead shutters 23, FIG. 2, delimiting the x-ray beam 5.

Figure 2:
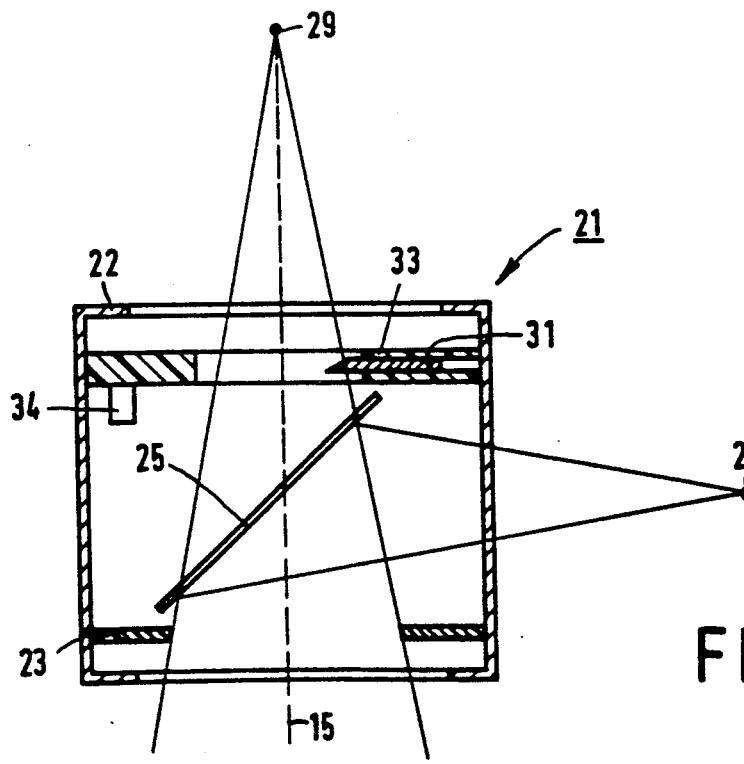
FIG. 2 shows a schematic representation of a collimating unit comprising filter means.

FIG. 2 schematically shows the collimating unit 21 which contains lead shutters 23 that can be moved away from and towards the central ray 15. In total there are four lead shutters 23 enclosing a rectangle. In order to get a visual indication of the collimating effect of the shutters 23 on the x-ray beam 7 an x-ray transparent mirror 25 is present in the collimating unit 21. A light source 27, that is in fact contained within the housing 22 of the collimating unit 21, is placed in a position corresponding to a focus 29 of the x-ray source 3. The projection of the lead shutters 23 onto the patient body 8 by the light source 27 corresponds to the field of view of the x-ray image. A filter 31, that comprises a wedge-shaped filter body 33 of for example copper or aluminum, is fixed in the housing 22 and can by means of a motor 34 be translated toward and away from the central ray 15 and be rotated around the central ray. The motor 34 can be activated by a user of the x-ray examination apparatus from a control panel 35, FIG. 2, connected to a side of the patient table 19. The filter 31 can also be placed below the lead shutters 23, or can be used in an x-ray examination apparatus in which no collimating unit 21 is present.

Figure 3:
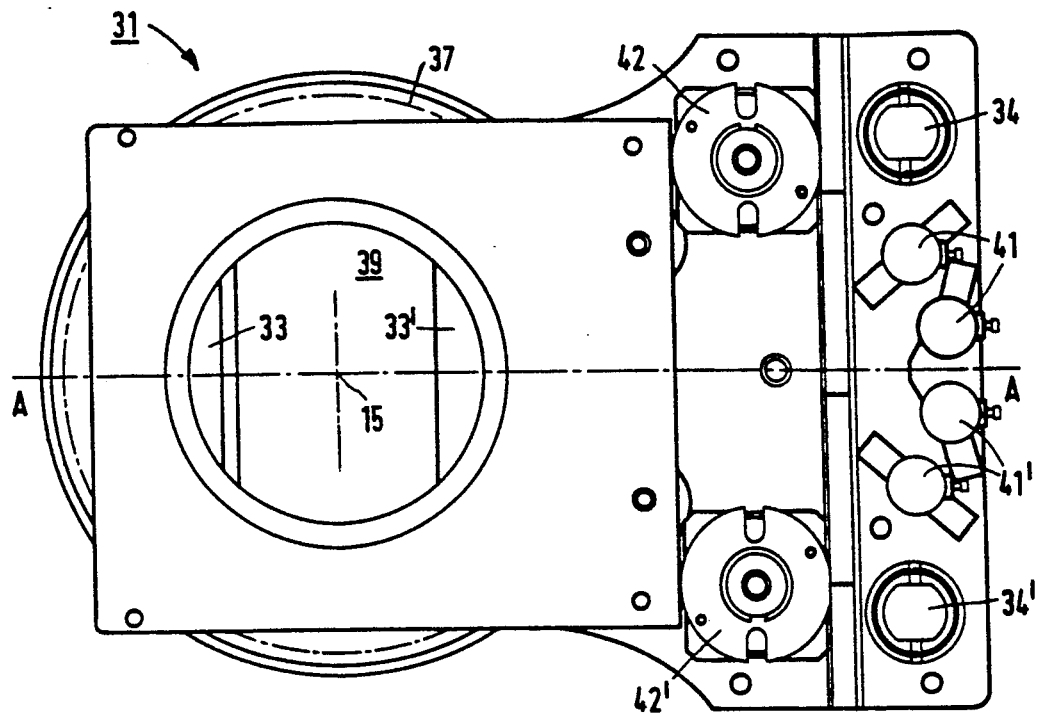
FIG. 3 shows a top view of the filter means according to the invention.
Figure 6:
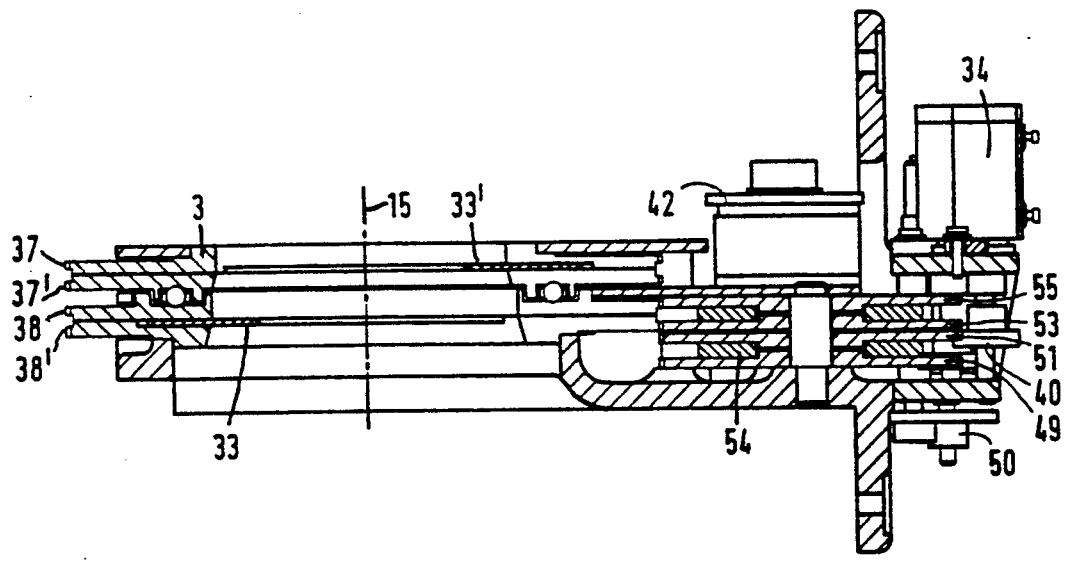
FIG. 6 shows a sectional view of the filter means of FIG. 3 along the line AA.

FIG. 3 shows a top view of the filter 31 in which the filter body 33 is held between two overlying disk-shaped holding members 37 and 37' (only one of which is shown in FIG. 3) and is movable within a central opening 39 through which the central ray 15 passes, the central ray being perpendicular to the plane of drawing. In the embodiment shown in this figure, two filters 31 are placed on top of one another such that two filter bodies 33 and 33' and four holding member 37, 37', 38 and 38' are present as shown in FIG. 6. The four holding members 37, 37', 38 and 38' can be rotated around the central ray 15 by two motors 34 and 34', FIG. 3. Connected to the motors 34 and 34' are four potentiometers 41 and 41' to determine the angular position of each holding member 37, 37', 38 and 38'. The signal of the potentiometers 41, 41' is for example supplied to a control unit for automatic positioning of the filter bodies 33 and 33' in the x-ray beam.

Figure 4:
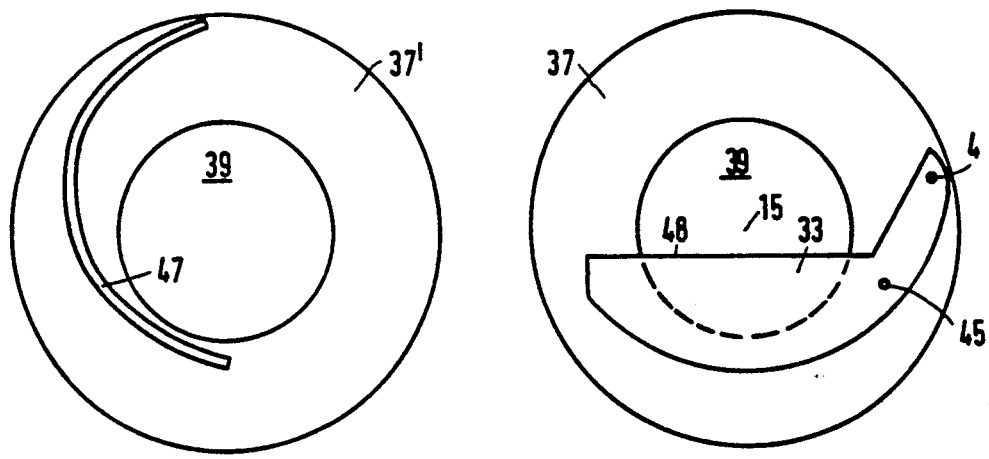
FIG. 4 shows the holding members and the filter body of the filter means according to the invention.

FIG. 4 shows the pair of holding members 37, 37' in a disassembled state. To the holding member 37 the filter body 33 is attached in a pivot-point 43 such as to be rotatable around an axis which runs through the pivot-point and which is perpendicular to the plane of drawing. The filter body 33 is provided with a pawl 45 that extends perpendicular to the plane of drawing and that fits in a curved radial groove 47 in the holding member 37'. The holding member 37' is to be placed on top of the holding member 37 such that the pawl 45 engages the groove 47. When, in the assembled state, the holding members are rotated with respect to one another, the groove 47 forces the filter body 33 to rotate around the pivot-point 43, whereby the filter body 33 covers or uncovers a part of the central opening 39. When both holding members rotate together, the straight edge 48 of the filter body 33 is rotated around the central ray 15 which extends perpendicular to the plane of drawing.

Figure 5:
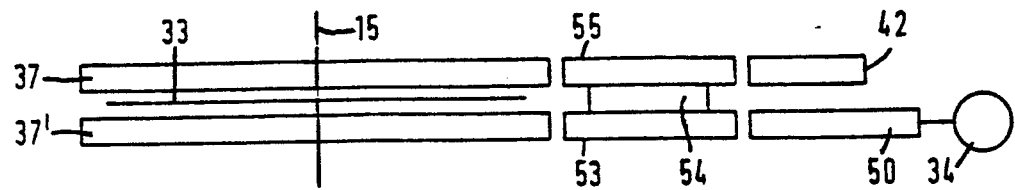
FIG. 5 shows a schematic representation of the coupling means, of the filter means

FIG. 5 shows a schematic representation of the coupling means, comprising a magnetically energizable brake 42 and two spur gears 53 and 55 that are mutually coupled by means of a layer of friction material 54 such as "Ferodo 3701 F" is supplied by the company Ferodo Limited (GB). When the brake 42 is not energized, the rotation of the spur gear 53, that is driven by the motor 34 and spur gear 50, is transmitted to the spur gear 55 by means of the layer of friction material 54. The layer of friction material 55 is fixedly connected to one of the spur gears 53 or 54. In this way the holding members 37 and 37' are jointly rotated around the central ray 15 with equal angular velocity such that the filter body 33 is rotated around the central ray 15. Energizing the brake 42, results in the spur gear being blocked. Since the coefficient of friction of the layer of friction material 54 is not large enough to prevent rotation of the spur gear 53, only the holding member 37' is rotated around the central ray 15 resulting in translation of the filter body 33.

FIG. 6 shows a sectional view of the filter 31. The spur gear 49 is via the spur gear 50 driven by the motor 34. Via the layer of friction material 54, the spur gear 51 is coupled to the spur gear 49. Via a transmission gear, not shown in this figure, the spur gears 49 and 51 cause the holding member 37 and 37' to rotate either jointly or relative to one another depending on whether the electromagnetic brake 42 has been energized or not. Rotation of the spur gear 51 is transmitted to a spindle 40 that is connected to a potentiometer 41 (not shown in this figure) for recording the angular position of the holding member 37. Likewise the spur gears 49, 53 and 55 are each connected to respective potentiometers 41 and 41'.

I claim:

1. X-ray examination apparatus comprising a frame to which are connected an x-ray source for emission of an x-ray beam and an x-ray detector that is placed opposite the x-ray source, and
    filter means between the x-ray source and the x-ray detector, the filter means comprising an x-ray absorbing filter body and drive means for positioning the filter body in the x-ray beam, the drive means comprise
    two holding members including guide means and having a central opening positioned around a central ray connecting the x-ray source and the x-ray detector, the filter body being between the holding members and being movably connected thereto via said guide means,
    a motor coupled to at least one holding member for rotation of the holding member around the central ray and
    coupling means for coupling and uncoupling the holding members including means for joint rotation of the holding members around the central ray for causing the filter body to be fixed relative to the holding member, and means for rotation of one of the holding members with respect to the other holding member for causing the filter body to move relative to the holding members via the guide means.

2. X-ray combination apparatus according to claim 1 wherein the holding members include first and second holding members, said members and the filter body are plate-shaped, the filter body being connected to the first holding member in a pivot-point such as to be pivotable in a plane parallel to the holding members, the guide means comprising a pawl on one of the filter body and second holding member and a groove in the other of said second holding member and in the filter body in which groove the pawl is guided.

3. X-ray examination apparatus according to claim 1 wherein the holding members have a toothed circular circumference.

4. X-ray examination apparatus according to claim 1 wherein the coupling means comprise a friction member for transmission of rotation of one holding member to the other holding member and a brake for locking one of the holding members.

5. X-ray examination apparatus according to claim 1 including two filter means provided as one integral unit which is placed near the x-ray source.

6. X-ray examination apparatus according to claim 3 including two filter means provided as one integral unit which is placed near the x-ray source.

7. X-ray examination apparatus according to claim 2 wherein the holding members have a toothed circular circumference.

8. X-ray examination apparatus according to claim 2 wherein the coupling means comprise a friction member for transmission of rotation of one holding member to the other holding member and a brake for locking one of the holding members.

9. X-ray examination apparatus according to claim 3 wherein the coupling means comprise a friction member for transmission of rotation of one holding member to the other holding member and a brake for locking one of the holding members.

10. X-ray examination apparatus according to claim 7 wherein the coupling means comprise a friction member for transmission of rotation of one holding member to the other holding member and a brake for locking one of the holding members.

11. X-ray examination apparatus according to claim 10 including two filter means provided as one integral unit which is placed near the x-ray source.

12. A filter construction according to claim 11 wherein the holding members include first and second holding members, said members and the filter body being plate shaped, the filter body being connected to the first holding member in a pivot point such as to be pivotable in a plane parallel to the holding members, the guide means comprising a pawl on one of the filter body and second holding member and a groove in the other of said second holding member and filter body in which the groove the pawl is guided.

13. X-ray examination apparatus according to claim 4 including two filter means provided as one integral unit which is placed near the x-ray source.

14. X-ray examination apparatus according to claim 2 including two filter means provided as one integral unit which is placed near the x-ray source.

15. A filter construction for use with an X-ray examination apparatus comprising:
    an X-ray absorbing filter body; and
    drive means for positioning the filter body in the X-ray beam;
    said drive means comprising:
        a pair of holding members including guide means and having a central opening positioned about a central ray emitted from an X-ray source to an X-ray detector, said filter body being between the holding members and moveably connected thereto via said guide means;
        a motor coupled to at lest one holding member for rotation of the at least one holding member around the central ray; and
        coupling means for coupling and uncoupling the holding members including means for joint rotation of the holding members around the central ray causing the filter body to be fixed relative to the holding members and means for rotation of one of the holding members with respect to the other holding member causing the filter body to move relative to the holding members via the guide means.

16. A filter construction according to claim 15 including two filter means provided as one integral unit adjacent to said X-ray source.

17. A filter construction according to claim 15 wherein the holding members have a toothed circular circumference.

18. A filter construction of claim 15 wherein the coupling means comprises a friction member for transmission of rotation of one holding member to the other holding member and a brake for locking one of the holding members.

* * * * *